(12) United States Patent
Shecterle et al.

(10) Patent No.: US 9,150,471 B2
(45) Date of Patent: Oct. 6, 2015

(54) METHODS AND APPARATUSES FOR TREATING A HYDROCARBON-CONTAINING FEED STREAM

(75) Inventors: David James Shecterle, Arlington Heights, IL (US); Jayant K. Gorawara, Buffalo Grove, IL (US); Henry Rastelli, Gurnee, IL (US)

(73) Assignee: UOP LLC, Des Plaines, IL (US)

( * ) Notice: Subject to any disclaimer, the term of this patent is extended or adjusted under 35 U.S.C. 154(b) by 100 days.

(21) Appl. No.: 13/284,512

(22) Filed: Oct. 28, 2011

(65) Prior Publication Data

US 2013/0109901 A1    May 2, 2013

(51) Int. Cl.
| | | |
|---|---|---|
| *C07C 7/13* | (2006.01) |
| *C10G 53/08* | (2006.01) |
| *C10G 25/03* | (2006.01) |
| *C10G 25/05* | (2006.01) |
| *C10G 33/06* | (2006.01) |

(52) U.S. Cl.
CPC . *C07C 7/13* (2013.01); *C10G 25/03* (2013.01); *C10G 25/05* (2013.01); *C10G 33/06* (2013.01); *C10G 53/08* (2013.01)

(58) Field of Classification Search
None
See application file for complete search history.

(56) References Cited

U.S. PATENT DOCUMENTS

| | | | |
|---|---|---|---|
| 4,028,223 A | 6/1977 | Hayes et al. | |
| 4,795,545 A | 1/1989 | Schmidt | |
| 4,827,076 A | 5/1989 | Kokayeff et al. | |
| 4,929,794 A | 5/1990 | Schmidt et al. | |
| 5,336,834 A | 8/1994 | Zarchy et al. | |
| 5,414,183 A | 5/1995 | Abrevaya et al. | |
| 5,705,730 A | 1/1998 | Zarchy et al. | |
| 7,651,550 B2 * | 1/2010 | Hawes et al. | .......... 95/135 |
| 8,163,068 B2 | 4/2012 | Shecterle et al. | |
| 2004/0192985 A1 | 9/2004 | Smith | |

OTHER PUBLICATIONS

Cvetanovic, R. J., et al., The Catalytic Properties of Molecular Sieves Containing Trapped Sulfur Free Radicals, 4th International Congress on Catalysis (Moscow Jun. 23-29, 1968), vol. 3, Jun. 23, 1968, p. 1082-1105.

Smith, D. L., Optimize solid-bed adsorption systems [used for dehydration and treating hydrocarbon gases and liquids], Hydrocarbon Processing (ISSN 0018-8190) vol. 75, No. 5, p. 129-132, May 1966.

* cited by examiner

*Primary Examiner* — Tam M Nguyen

(57) ABSTRACT

Embodiments of methods and apparatuses for treating a hydrocarbon-containing feed stream are provided. The method comprises the steps of contacting the hydrocarbon-containing feed stream comprising $C_4$, $C_5$, $C_6$, and/or $C_7$ hydrocarbons, water, and contaminants with a Linde Type A molecular sieve at dehydration conditions effective to remove water and form a dehydrated feed stream. The contaminants comprise oxygenates, sulfur compounds, or combinations thereof. The dehydrated feed stream is contacted with a sodium faujisite molecular sieve having a silica/alumina molar ratio of from about 2 to about 2.5 at absorption conditions effective to remove the contaminants and form a dehydrated contaminant-depleted feed stream.

19 Claims, 2 Drawing Sheets

METHODS AND APPARATUSES FOR TREATING A HYDROCARBON-CONTAINING FEED STREAM

TECHNICAL FIELD

The present invention relates generally to methods and apparatuses for treating a hydrocarbon-containing feed stream, and more particularly relates to methods and apparatuses for treating a hydrocarbon-containing feed stream including removing water and other contaminants, such as oxygenates and/or sulfur compounds, from the feed stream.

BACKGROUND

The removal of water and other contaminants, such as oxygenates and/or sulfur compounds, from light hydrocarbons is often performed to produce a clean hydrocarbon product. The clean hydrocarbon product can be further treated using catalytic reactions, such as catalytic isomerization, to produce other hydrocarbons, increase octane, improve the product value, and/or the like. In particular, catalysts that are typically used for catalytic isomerization and other catalytic reactions are very sensitive to water, oxygenates, and sulfur compounds, which can cause deactivation of the catalyst, thereby reducing catalyst life, increasing the number of catalyst regenerations, and/or requiring complete replacement of the catalyst.

One conventional process for removing water and other contaminants from light hydrocarbons employs a bed arrangement that contains a relatively large pore molecular sieve as an absorbent material. A light hydrocarbon stream is passed through the bed arrangement and the molecular sieve absorbs much of the water and other contaminants from the stream to produce a clean hydrocarbon product. As the molecular sieve removes the undesirable components from the stream, its surface and pores become saturated with water and to a lesser extent the other contaminants, causing the molecular sieve to become less active. To restore its activity, the molecular sieve is regenerated at higher temperatures to help remove the absorbed water and other contaminants. Although water is readily removed from the molecular sieve during regeneration, the other contaminants tend to remain and react at the higher temperatures to form a gummy residue. The gummy residue steadily builds up during each additional regeneration, plugging the pores and causing premature permanent deactivation of the molecular sieve. Since regeneration at this point is no longer effective to restore activity, the molecular sieve needs to be replaced, which is expensive and time consuming.

Accordingly, it is desirable to provide methods and apparatuses for treating a hydrocarbon-containing feed stream using an absorbent material(s) to remove water and other contaminants to produce a clean hydrocarbon product without causing premature permanent deactivation of the absorbent material(s). Moreover, it is desirable to provide methods and apparatuses for treating a hydrocarbon-containing feed stream to produce a clean hydrocarbon product using an absorbent material(s) that may be frequently regenerated to restore activity without causing a steady buildup of gummy residue on the absorbent material(s). Furthermore, other desirable features and characteristics of the present invention will become apparent from the subsequent detailed description and the appended claims, taken in conjunction with the accompanying drawings and this background.

BRIEF SUMMARY

Methods and apparatuses for treating a hydrocarbon-containing feed stream are provided herein. In accordance with an exemplary embodiment, a method for treating a hydrocarbon-containing feed stream comprises the steps of contacting the hydrocarbon-containing feed stream comprising $C_4$, $C_5$, $C_6$, and/or $C_7$ hydrocarbons, water, and contaminants with a Linde Type A molecular sieve at dehydration conditions effective to remove water and form a dehydrated feed stream. The contaminants comprise oxygenates, sulfur compounds, or combinations thereof. The dehydrated feed stream is contacted with a sodium faujisite molecular sieve having a silica/alumina molar ratio of from about 2 to about 2.5 at absorption conditions effective to remove the contaminants and form a dehydrated contaminant-depleted feed stream.

In accordance with another exemplary embodiment, a method for treating a hydrocarbon-containing feed stream is provided. The method comprises the steps of introducing the hydrocarbon-containing feed stream comprising $C_4$, $C_5$, $C_6$, and/or $C_7$ hydrocarbons, water, and contaminants to a regenerative dehydration zone that comprises a Linde Type A molecular sieve at dehydration conditions effective to remove water and form a dehydrated feed stream and a spent Linde Type A molecular sieve. The contaminants comprise oxygenates, sulfur compounds, or combinations thereof. The spent Linde Type A molecular sieve is regenerated in the regenerative dehydration zone at regenerative conditions effective to form a regenerated Linde Type A molecular sieve. At least a portion of the dehydrated feed stream is introduced to a guard bed that contains sodium faujisite molecular sieve having a silica/alumina molar ratio of from about 2 to about 2.5 and that is operating at absorption conditions effective to remove the contaminants and form a dehydrated contaminant-depleted feed stream.

In accordance with another exemplary embodiment, an apparatus for treating a hydrocarbon-containing feed stream is provided. The apparatus comprises a first dryer containing a first quantity of Linde Type A molecular sieve. The first dryer is configured to receive the hydrocarbon-containing feed stream comprising $C_4$, $C_5$, $C_6$, and/or $C_7$ hydrocarbons, water, and contaminants and to operate in a first dehydration mode at dehydration conditions effective to remove water and form a dehydrated feed stream and a first quantity of spent Linde Type A molecular sieve. The contaminants comprise oxygenates, sulfur compounds, or combinations thereof. A guard bed contains sodium faujisite molecular sieve having a silica/alumina molar ratio of from about 2 to about 2.5 and is configured to receive at least a portion of the dehydrated feed stream and to operate at absorption conditions effective to remove the contaminants and form a dehydrated contaminant-depleted feed stream.

BRIEF DESCRIPTION OF THE DRAWINGS

The present invention will hereinafter be described in conjunction with the following drawing figures, wherein like numerals denote like elements, and wherein.

DETAILED DESCRIPTION

Figure 1:
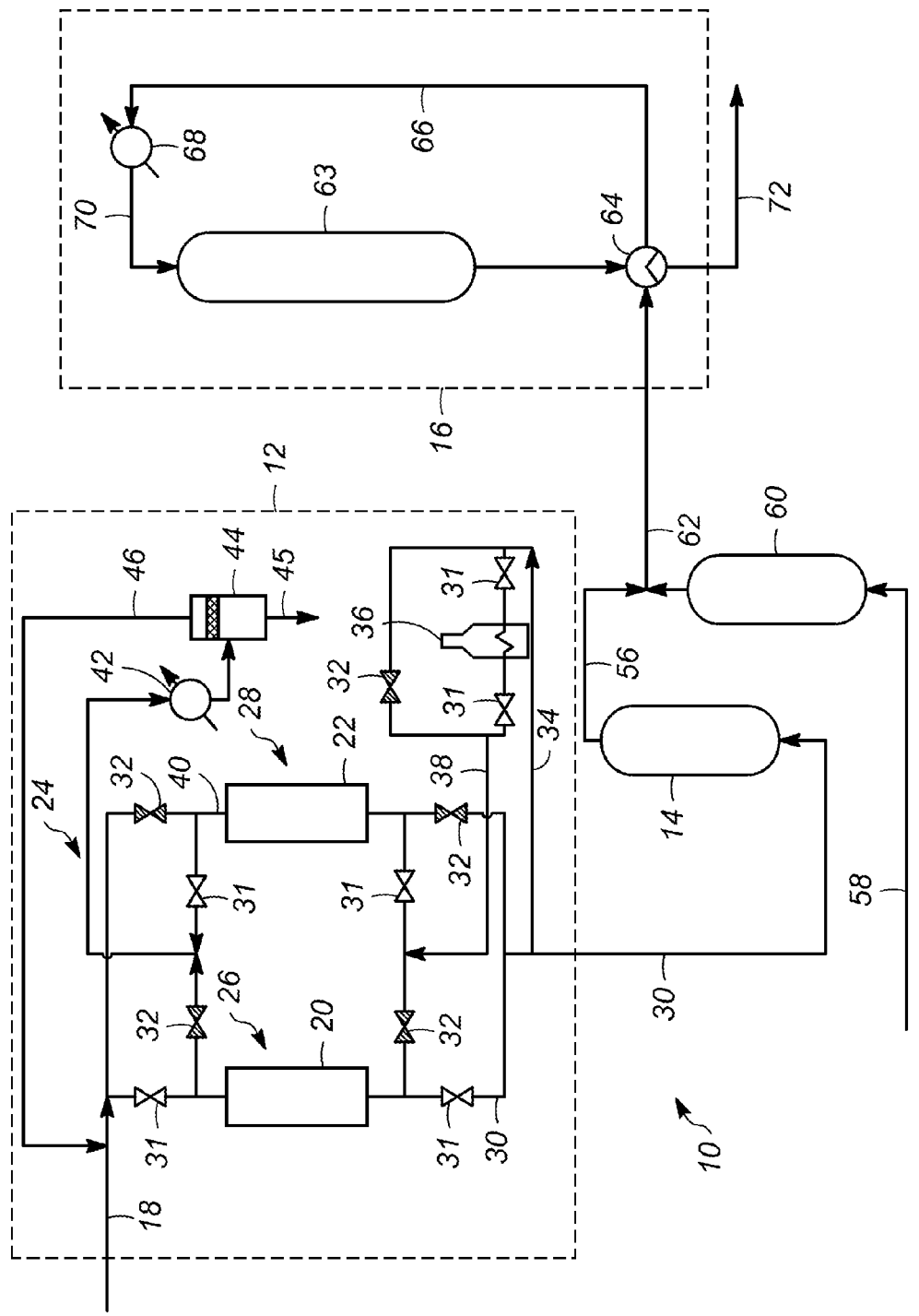
FIG. 1 schematically illustrates an apparatus for treating a hydrocarbon-containing feed stream in accordance with an exemplary embodiment.

The following Detailed Description is merely exemplary in nature and is not intended to limit the invention or the application and uses of the invention. Furthermore, there is no intention to be bound by any theory presented in the preceding background or the following detailed description.

Various embodiments contemplated herein relate to methods and apparatuses for treating a hydrocarbon-containing feed stream. Unlike the prior art, the exemplary embodiments taught herein include contacting a hydrocarbon-containing feed stream comprising $C_4$, $C_5$, $C_6$, and/or $C_7$ hydrocarbons, water, and contaminants, such as oxygenates and/or sulfur compounds, with a Linde Type A molecular sieve, such as, for example, a Linde Type A molecular sieve, at dehydration conditions effective to selectively remove water from the feed stream preferably without removing the contaminants to form a dehydrated feed stream. As used herein, $C_x$ means hydrocarbon molecules that have "X" number of carbon atoms. As will be discussed in further detail below, the Linde Type A molecular sieve is a porous zeolitic molecular sieve that has a relatively small pore size. The inventors have found that the relatively small pore size of the Linde Type A molecular sieve promotes selectively absorbing water from the feed stream by allowing the smaller water molecules to readily enter into the small pores while the larger contaminant molecules, e.g., oxygenate and/or sulfur compound molecules, are effectively blocked from entering the small pores. Therefore, as the Linde Type A molecular sieve loses its activity and becomes spent, the surface and pores of the spent Linde Type A molecular sieve are saturated with water but remain substantially free of the contaminants.

In an exemplary embodiment, the spent Linde Type A molecular sieve is regenerated to restore its activity. The spent Linde Type A molecular sieve is regenerated at regenerative conditions that include a relatively high temperature to help drive off the absorbed water and form a regenerated Linde Type A molecular sieve. Since the spent Linde Type A molecular sieve is substantially free of the contaminants, a gummy residue is preferably not formed on the molecular sieve from exposure to the higher temperatures during regeneration. Therefore, the Linde Type A molecular sieve can be regenerated frequently as required restoring its activity without forming a buildup of gummy residue that may otherwise cause premature permanent deactivation of the molecular sieve.

The dehydrated feed stream is then contacted with sodium faujisite molecular sieve having a silica/alumina molar ratio of from about 2 to about 2.5, such as, for example, 13X molecular sieve, at absorption conditions effective to remove the contaminants and form a dehydrated contaminant-depleted feed stream. As will be discussed in further detail below, the sodium faujisite molecular sieve having a silica/alumina molar ratio of from about 2 to about 2.5 is a porous zeolitic molecular sieve having a relatively large pore size of up to about 10 Å, for example. The relatively large pore size of the sodium faujisite molecular sieve promotes absorption of the contaminants from the dehydrated feed stream by allowing the larger contaminant molecules to readily enter into the large pores. Because the dehydrated feed stream is substantially free of water, the surface and pores of the sodium faujisite molecular sieve remain substantially free of water, which the inventors have found prolongs the activity of the molecular sieve. Preferably, the sodium faujisite molecular sieve is not regenerated and therefore, a gummy residue that may otherwise be formed from exposing the contaminants to higher temperatures during regeneration is not produced.

In an exemplary embodiment, the dehydrated contaminant-depleted feed stream is a clean hydrocarbon product that is suitable for further treatment using a catalytic reaction. In one specific example of this embodiment, the dehydrated contaminant-depleted feed stream is contacted with an isomerization catalyst in the presence of hydrogen at isomerization conditions effective to form an isomerization effluent. The isomerization effluent comprises branched paraffins, normal paraffins, and naphthenes.

Referring to FIG. 1, a schematic depiction of an apparatus 10 for treating hydrocarbons in accordance with an exemplary embodiment is provided. As illustrated, the apparatus 10 comprises a regenerative dehydration zone 12 that is in fluid communication with a guard bed 14 and a paraffin isomerization zone 16 that is in fluid communication with the guard bed 14. A hydrocarbon-containing feed stream 18 is introduced to the regenerative dehydration zone 12. The hydrocarbon-containing feed stream 18 comprises $C_4$, $C_5$, $C_6$, and/or $C_7$ hydrocarbons, water, and contaminants. Some examples of $C_4$, $C_5$, $C_6$, and/or $C_7$ hydrocarbons include, but are not limited to, paraffins, olefins, naphthenes, and/or aromatics. Some examples of contaminants include, but are not limited to, oxygenates such as carbon dioxide, ethanol, methanol, tertiary butyl alcohol, dimethyl ether, methyl tertiary butyl ether, and the like; and sulfur compounds such as hydrogen sulfide, mercaptans, carbonyl sulfide, and the like. In one example, the hydrocarbon-containing feed stream 18 is formed upstream at least in part by a raffinate stream from an aromatics extraction unit. The raffinate stream is highly paraffinic and contains trace amounts of sulfolane, which is an extraction solvent used in the aromatics extraction unit. Sulfolane is a contaminant that is both an oxygenate and a sulfur compound, and is particularly poisonous to many isomerization catalysts that may be used downstream in the paraffin isomerization zone 16, as will be discussed in further detail below. In an exemplary embodiment, sulfolane is present in the hydrocarbon-containing feed stream 18 in an amount of about 1 weight part per million (wt. ppm) or greater.

The regenerative dehydration zone 12 comprises a first dryer 20 and a second dryer 22 that are in fluid communication with each other. Each of the dryers contains Linde Type A molecular sieve, such as Linde 3A molecular sieve. As used herein, the term "molecular sieve" is defined as a class of adsorptive desiccants that are highly crystalline in nature, distinct from amorphous materials such as gamma-alumina. As used herein, the terms "absorb," "absorbed," "absorbing," "absorptive," and "absorption" are used broadly and are to be understood to also include "adsorb," "adsorbed," "adsorbing," "adsorptive," and/or "adsorption." Various types of molecular sieves include aluminosilicate materials commonly known as zeolites. As used herein, the term "zeolite" in general refers to a group of naturally occurring and synthetic hydrated metal aluminosilicates, many of which are crystalline in structure. There are, however, significant differences between the various synthetic and natural materials, such as differences in chemical composition, crystal structure and physical properties. The zeolites occur as agglomerates of fine crystals or are synthesized as fine powders and are preferably tableted or pelletized for large-scale adsorption uses. Zeolites are characterized by having pore openings of uniform dimensions in which the pore size may be varied by employing different metal cations using ion exchange as is well known in the art. As used herein, "pore size" is defined as the free diameter of the appropriate silicate ring in the zeolite structure. A Linde Type A molecular sieve (e.g. Linde 3A molecular sieve) is a porous zeolitic material having a Linde Type A structure and is described in *The Atlas of Zeolite Structure Types* by W. M. Meier. In the case of Linde 3A molecular sieve, the Linde Type A material has been potassium ion exchanged to reduce the pore size to about 3 to about 3.5 Å. In particular, Linde Type A molecular sieve is built by linking sodalite cages through double four-rings to create a cavity accessible to molecules no larger than water via a three-dimensional eight-ring channel system.

As illustrated, the regenerative dehydration zone 12 is configured for "closed loop product regeneration." The first and second dryers 20 and 22 are configured as a swing bed arrangement 24 in which one of the first and second dryers 20 and 22 is in a dehydration mode 26 and the other of the first and second dryers 20 and 22 is in a regenerative mode 28. In particular, when a first plurality of valves 31 are in an opened position and a second plurality of valves 32 are in a closed position, the first dryer 20 is in the dehydration mode 26 and the second dryer 22 is in the regenerative mode 28. Alternatively, when the first plurality of valves 31 are in the closed position and the second plurality of valves 32 are in the opened position, the first dryer 20 is in the regenerative mode 28 and the second dryer 22 is in the dehydration mode 26.

As illustrated, the first dryer 20 in the dehydration mode 26 receives the hydrocarbon-containing feed stream 18 and is operating at dehydration conditions. In an exemplary embodiment, the dehydration conditions include a temperature of from about 0 to about 60° C., preferably of about 0 to about 50° C., and more preferably of about ambient, and a pressure so as to maintain a liquid phase, such as, for example, of from about 350 to about 4200 kPa. The hydrocarbon-containing feed stream 18 contacts the Linde Type A molecular sieve and water is selectively absorbed into the molecular sieve to form a dehydrated feed stream 30. As the surface and pores of the Linde Type A molecular sieve become saturated with water, the molecular sieve loses activity and forms spent Linde Type A molecular sieve. Preferably, the dehydrated feed stream 30 comprises water that is present in an amount of about 1 wt. ppm or less, and the contaminants remain present at about the same level as in the hydrocarbon-containing feed stream 18. As such, the spent Linde Type A molecular sieve is primarily saturated with water and remains substantially free of the contaminants.

In the regenerative mode 28, the second dryer 22, which was previously in the dehydration mode 26 as discussed in the foregoing paragraph with respect to the first dryer 20, contains spent Linde Type A molecular sieve. A portion 34 of the dehydrated feed stream 30 is passed through a heater 36 and is heated to a temperature preferably of from about 200 to about 320° C. to form a heated product regeneration stream 38. In an exemplary embodiment, the heated product regeneration stream 38 is introduced to the second dryer 22 that is operating at regenerative conditions including a temperature of from about 200 to about 320° C. The heated product regeneration stream 38 contacts the spent Linde Type A molecular sieve and removes water to restore activity to the molecular sieve, forming regenerated Linde Type A molecular sieve and a spent product regeneration stream 40. The spent product regeneration stream 40 is passed through a cooler 42 where it is cooled to a temperature of about 60° C. or less and is introduced to a separation unit 44. The separation unit 44 separates water from the spent product regeneration stream 40, forming a water waste stream 45 and a hydrocarbon-containing stream 46 that is combined with the hydrocarbon-containing feed stream 18.

Figure 2:
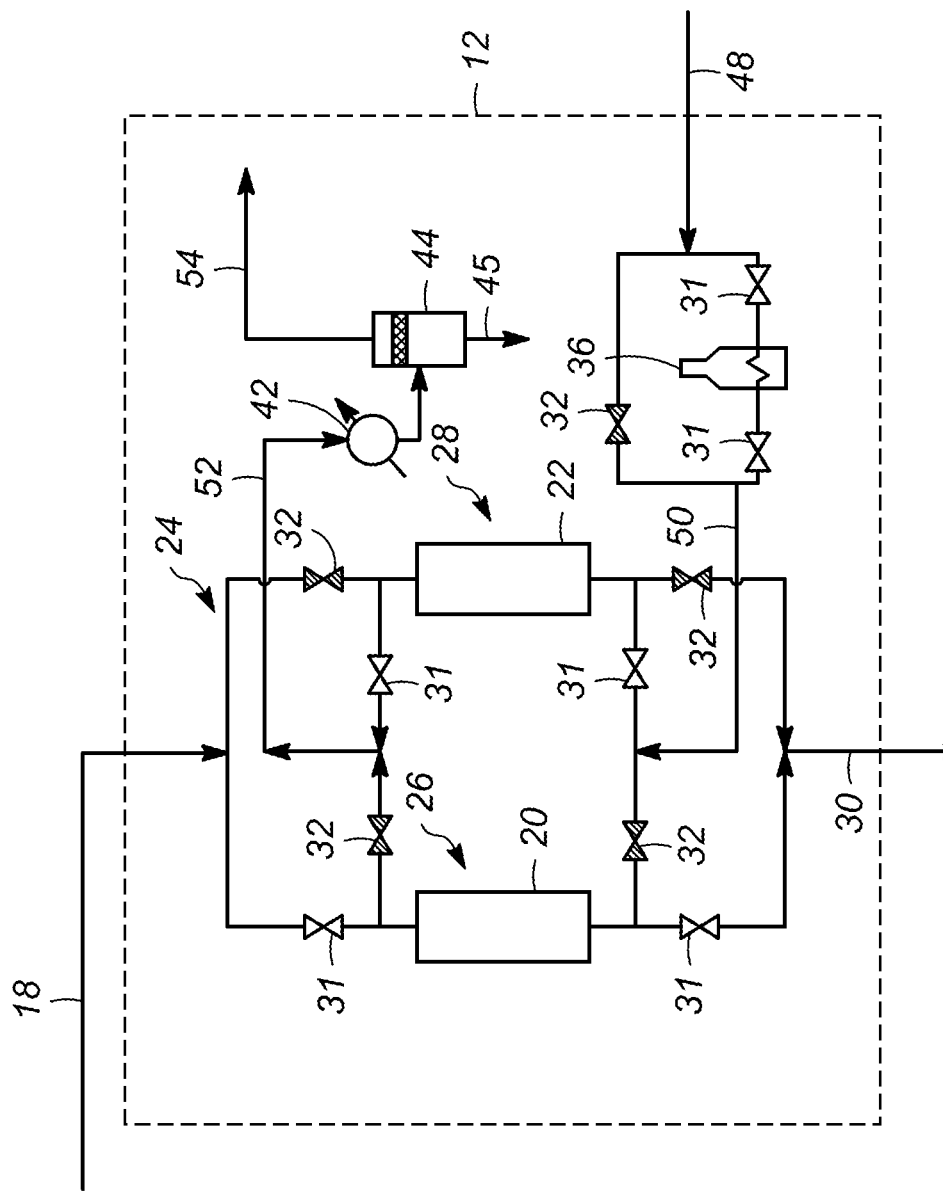
FIG. 2 schematically illustrates a regenerative dehydration zone for treating a hydrocarbon-containing feed stream in accordance with an exemplary embodiment.

In an alternative embodiment and as illustrated in FIG. 2, the regenerative dehydration zone 12 is configured for "open loop regeneration." In particular, the first and second dryers 20 and 22 are configured as a swing bed arrangement 24 and operate as discussed above but instead of using a portion of the dehydrated feed stream 30 for the regenerative mode 28, a fresh regenerant stream 48 is introduced to the regenerative dehydration zone 12 and is used for regeneration of the spent Linde Type A molecular sieve. The fresh regenerant stream 48 is preferably a light hydrocarbon stream (e.g. $C_4$-$C_7$ hydrocarbons) that contains little or no water (e.g. 1 wt. ppm or less).

The fresh regenerant stream 48 is passed through the heater 36 and is heated to a temperature of from about 200 to about 320° C. to form a heated regenerant stream 50. As illustrated, the heated regenerant stream 50 is introduced to the second dryer 22 that is in the regenerative mode 28 and is operating at the regenerative conditions. The heated regenerant stream 50 contacts the spent Linde Type A molecular sieve and removes water to restore activity to the molecular sieve, forming regenerated Linde Type A molecular sieve and spent regenerant 52. The spent regenerant 52 is passed through a cooler 42 where it is cooled to a temperature of about 60° C. or less and introduced to a separation unit 44. The separation unit 44 separates the water from the spent regenerant 52, forming a water waste stream 45 and a water-depleted regenerant stream 54 that may be recycled or removed from the regenerative dehydration zone 12.

Referring back to FIG. 1, the dehydrated feed stream 30 is removed from the regenerative dehydration zone 12 and is introduced to the guard bed 14. The guard bed 14 contains sodium faujisite molecular sieve having a silica/alumina molar ratio of from about 2 to about 2.5, such as 13X molecular sieve, which is described in *The Atlas of Zeolite Structure Types* by W. M. Meier. In particular, 13X molecular sieve is a porous synthetic crystalline zeolitic material having the following composition:

$$1.0+/-0.2Na_2O:1.00Al_2O_3:2.5+/-0.5SiO_2$$

plus water of hydration. 13X molecular sieve has a cubic crystalline structure that is characterized by a three-dimensional network with mutually connected intracrystalline voids accessible through pore openings that will admit molecules with critical dimensions of up to about 10 Å (e.g. 10 Å pore size). The sodium faujisite molecular sieve will permit the absorption of the larger contaminant molecules, such as, for example, oxygenates and sulfur compounds.

The guard bed 14 is operating at absorption conditions and the dehydrated feed stream 30 contacts the sodium faujisite molecular sieve to remove the contaminants and form a dehydrated contaminant-depleted feed stream 56. In an exemplary embodiment, the absorption conditions include a temperature of from about 0 to about 60° C., and a pressure so as to maintain a liquid phase, such as, for example, of from about 350 to about 4,200 kPa. Preferably, the amount of contaminants present in the dehydrated contaminant-depleted feed stream 56 is about 1 wt. ppm or less, and more preferably of about 0.5 wt. ppm or less, and most preferably of about 0.1 wt. ppm or less. In a specific example of this embodiment, the amount of sulfolane present in the dehydrated contaminant-depleted feed stream 56 is about 0.1 wt. ppm or less.

In an exemplary embodiment, a hydrogen feed stream 58 is passed through a third dryer 60 to remove water and is combined with the dehydrated contaminant-depleted feed stream 56 to form a combined streams 62. The combined streams 62 is introduced to the paraffin isomerization zone 16 that comprises an isomerization reactor 63. As illustrated, the combined stream 62 is passed through a heat exchanger 64 to partially heat the combined stream 62 to a temperature preferably of from about 65 to about 175° C. to form a partially heated combined stream 66. The partially heated combined stream 66 is passed through a heater 68 and heated to a temperature preferably of from about 95 to about 205° C. to form a heated combined feed stream 70.

The heated combined feed stream 70 is introduced to the isomerization reactor 63. In an exemplary embodiment, the isomerization reactor 63 is configured as a fixed-bed catalytic reactor operating at isomerization conditions including a temperature of from about 95 to about 205° C. and contains a high-activity chloride-promoted isomerization catalyst. The heated combined feed stream 70 contacts the isomerization catalyst to form an isomerization effluent 72 that contains branched paraffins and the like, such as, for example, isobutane, isopentane, and the like. The isomerization effluent 72 is passed through the heat exchanger 64 and is removed from the paraffin isomerization zone 16 for further processing, such as, for example, fractionation, separation, scrubbing, and the like.

Accordingly, methods and apparatuses for treating a hydrocarbon-containing feed stream have been described. The various embodiments comprise contacting a hydrocarbon-containing feed stream comprising $C_4$, $C_5$, $C_6$, and/or $C_7$ hydrocarbons, water, and contaminants with Linde Type A molecular sieve at dehydration conditions to selectively remove water from the feed stream to form a dehydrated feed stream and spent Linde Type A molecular sieve. The spent Linde Type A molecular sieve is regenerated at regenerative conditions that include a relatively high temperature to help drive off the absorbed water and form a regenerated Linde Type A molecular sieve. Since the spent Linde Type A molecular sieve is substantially free of the contaminants, a gummy residue is preferably not formed on the molecular sieve from exposure to the higher temperatures during regeneration. Therefore, the Linde Type A molecular sieve can be regenerated frequently as required restoring its activity without forming a buildup of gummy residue that may otherwise cause premature permanent deactivation of the molecular sieve. The dehydrated feed stream is then contacted with sodium faujisite molecular sieve having a silica/alumina molar ratio of from about 2 to about 2.5 at absorption conditions to remove the contaminants and form a dehydrated contaminant-depleted feed stream. Because the dehydrated feed stream is substantially free of water, the surface and pores of the sodium faujisite molecular sieve remain substantially free of water, which has been found to prolong the activity of the molecular sieve. Preferably, the sodium faujisite molecular sieve is not regenerated and therefore, a gummy residue that may otherwise be formed from exposing the contaminants to higher temperatures during regeneration is not produced.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for treating a hydrocarbon-containing feed stream comprising $C_4$, $C_5$, $C_6$, and/or $C_7$ hydrocarbons, water, and residue-forming contaminants including oxygenates, sulfur compounds, or combinations thereof, the method comprising the steps of:

selectively removing the water from the hydrocarbon-containing feed stream by contacting the hydrocarbon-containing feed stream with a regenerated Linde Type A molecular sieve and selectively absorbing the water with the regenerated Linde Type A molecular sieve to form a water-saturated molecular sieve substantially free of the contaminants and a dehydrated feed stream having a water content of about 1 wt. ppm or less and a residue-forming contaminant content substantially equal to a residue-forming contaminant content of the hydrocarbon-containing feed stream;

separating the water-saturated molecular sieve from the dehydrated feed stream;

regenerating the water-saturated molecular sieve at regenerative conditions effective to form the regenerated Linde Type A molecular sieve;

removing the residue-forming contaminants from the dehydrated feed stream by contacting the dehydrated feed stream with a non-regenerated sodium faujisite molecular sieve having a silica/alumina molar ratio of from about 2 to about 2.5 to form a dehydrated contaminant-depleted feed stream and a spent sodium faujisite molecular sieve, and replacing the spent sodium faujisite molecular sieve with a new non-regenerated sodium faujisite molecular sieve, wherein contacting with the regenerated Linde Type A molecular sieve is performed within a dryer unit that does not include the non-regenerated sodium faujisite molecular sieve.

2. The method of claim 1, wherein the step of selectively removing the water from the hydrocarbon-containing feed stream includes contacting the hydrocarbon-containing feed stream with a Linde 3A molecular sieve.

3. The method of claim 1, wherein the step of selectively removing the water from the hydrocarbon-containing feed stream includes contacting the hydrocarbon-containing feed stream with the Linde Type A molecular sieve at dehydration conditions that include a temperature of from about 0 to about 60° C. and a pressure such that the feed stream is in a liquid phase.

4. The method of claim 1, wherein the step of removing the contaminants from the dehydrated feed stream includes forming the dehydrated contaminant-depleted feed stream having a contaminant content of about 1 wt. ppm or less.

5. The method of claim 1, wherein the step of removing the contaminants from the dehydrated feed stream includes forming the dehydrated contaminant-depleted feed stream having a contaminant content of about 0.1 wt. ppm or less.

6. The method of claim 1, wherein the step of removing the contaminants from the dehydrated feed stream includes contacting the dehydrated feed stream with the sodium faujisite molecular sieve at absorption conditions that include a pressure such that the dehydrated feed stream is in a liquid phase.

7. The method of claim 1, wherein the step of removing the contaminants from the dehydrated feed stream includes removing sulfolane, hydrogen sulfide, mercaptans, carbonyl sulfide, carbon dioxide, ethanol, methanol, tertiary butyl alcohol, dimethyl ether, methyl tertiary butyl ether, or combinations thereof from the dehydrated feed stream.

8. The method of claim 1, wherein the step of removing the contaminants from the dehydrated feed stream includes removing sulfolane present in the dehydrated feed stream in a first amount of about 1 wt. ppm or greater to form the dehydrated contaminant-depleted feed stream with sulfolane present in a second amount of about 0.1 wt. ppm or less.

9. The method of claim 1, wherein the step of regenerating the water-saturated molecular sieve includes contacting the water-saturated molecular sieve with a portion of the dehydrated feed stream at the regenerative conditions to form the regenerated Linde Type A molecular sieve.

10. The method of claim 1, wherein the step of regenerating the water-saturated molecular sieve includes contacting the water-saturated molecular sieve with a regenerant at the regenerative conditions to form the regenerated Linde Type A molecular sieve.

11. The method of claim 1, wherein the step of regenerating the water-saturated molecular sieve includes regenerating the water-saturated molecular sieve at the regenerative conditions that includes a temperature of from about 200 to about 320° C.

12. A method for treating a hydrocarbon-containing feed stream, the method comprising the steps of:
   introducing the hydrocarbon-containing feed stream comprising $C_4$, $C_5$, $C_6$, and/or $C_7$ hydrocarbons, water, and residue-forming contaminants to a regenerative dehydration zone that comprises a Linde Type A molecular sieve at dehydration conditions effective to remove water and to form a dehydrated feed stream comprising the hydrocarbons and the residue-forming contaminants and to form a spent Linde Type A molecular sieve substantially free of the contaminants, wherein the residue-forming contaminants comprise oxygenates, sulfur compounds, or combinations thereof;
   removing the dehydrated feed stream from the regenerative dehydration zone;
   regenerating the spent Linde Type A molecular sieve in the regenerative dehydration zone at regenerative conditions substantially free of the residue-forming contaminants effective to form a regenerated Linde Type A molecular sieve;
   introducing at least a portion of the dehydrated feed stream to a guard bed, separate and apart from the dehydration zone, that contains a non-regenerated sodium faujisite molecular sieve having a silica/alumina molar ratio of from about 2 to about 2.5 and that is operating at absorption conditions effective to remove the residue-forming contaminants and form a dehydrated contaminant-depleted feed stream,
   continuing to utilize non-regenerated sodium faujisite molecular sieve thereby preventing production of gummy residue otherwise formed from exposing contaminants in a sodium faujisite molecular sieve to higher temperatures during regeneration; and
   wherein the dehydration zone does not include sodium faujisite molecular sieve.

13. The method of claim 12, wherein the step of introducing the hydrocarbon-containing feed stream includes:
   introducing the hydrocarbon-containing feed stream to a first dryer of the regenerative dehydration zone, wherein the first dryer contains a first quantity of the Linde Type A molecular sieve and is operating in a dehydration mode at the dehydration conditions to form the dehydrated feed stream and a first quantity of the spent Linde Type A molecular sieve, and wherein the step of regenerating includes:
   introducing a first portion of the dehydrated feed stream from the first dryer to a second dryer of the regenerative dehydration zone, wherein the second dryer contains a second quantity of the spent Linde Type A molecular sieve and is operating in a regenerative mode at the regenerative conditions to regenerate the second quantity of the spent Linde Type A molecular sieve to form a first quantity of the regenerated Linde Type A molecular sieve.

14. The method of claim 12, wherein the step of introducing the hydrocarbon-containing feed stream includes:
   introducing the hydrocarbon-containing feed stream to a first dryer of the regenerative dehydration zone, wherein the first dryer contains a first quantity of the Linde Type A molecular sieve and is operating in a dehydration mode at the dehydration conditions to form the dehydrated feed stream and a first quantity of the spent Linde Type A molecular sieve; and wherein the step of regenerating includes:
   introducing a regenerant to a second dryer of the regenerative dehydration zone, wherein the second dryer contains a second quantity of the spent Linde Type A molecular sieve and is operating in a regenerative mode at the regenerative conditions to regenerate the second quantity of the spent Linde Type A molecular sieve to form a first quantity of the regenerated Linde Type A molecular sieve.

15. The method of claim 12, further comprising the step of:
   introducing the dehydrated contaminant-depleted feed stream to an isomerization reactor that contains an isomerization catalyst in the presence of hydrogen and that is operating at isomerization conditions effective to form an isomerization effluent that comprises branched paraffins, olefins, naphthenes, aromatics, or combinations thereof.

16. The method of claim 12, wherein:
   removing the dehydrated feed stream from the regenerative dehydration zone and introducing at least a portion of the dehydrated feed stream to a guard bed comprises passing the dehydrated feed stream from the regenerative dehydration zone to the guard bed in a first direction; and
   regenerating the spent Linde Type A molecular sieve in the regenerative dehydration zone comprises introducing a regenerant between the guard bed and the regenerative dehydration zone and passing the regenerant through the dehydration zone in a second direction opposite to the first direction, wherein the regenerant bypasses the guard bed.

17. The method of claim 12, wherein:
   removing the dehydrated feed stream from the regenerative dehydration zone and introducing at least a portion of the dehydrated feed stream to a guard bed comprises opening a first valve between the regenerative dehydration zone and the guard bed and passing the dehydrated feed stream from the regenerative dehydration zone to the guard bed in a first direction; and
   regenerating the spent Linde Type A molecular sieve in the regenerative dehydration zone comprises closing the first valve and introducing a regenerant between the first valve and the regenerative dehydration zone and passing the regenerant through the dehydration zone in a second direction opposite to the first direction, wherein the regenerant bypasses the guard bed.

18. The method of claim 12, wherein:
   introducing the hydrocarbon-containing feed stream comprising C4, C5, C6, and/or C7 hydrocarbons, water, and contaminants to a regenerative dehydration zone and removing the dehydrated feed stream from the regenerative dehydration zone comprises selectively passing the hydrocarbon-containing feed stream through a dryer in a first direction;
   introducing at least a portion of the dehydrated feed stream to a guard bed comprises passing the dehydrated feed stream through a valve in an open configuration to the guard bed; and regenerating the spent Linde Type A molecular sieve in the regenerative dehydration zone comprises passing a regenerant through the dryer in a second direction opposite to the first direction, wherein flow of the regenerant to the guard bed is prevented by the valve in a closed configuration.

19. The method of claim 12, wherein:

removing the dehydrated feed stream from the regenerative dehydration zone and introducing at least a portion of the dehydrated feed stream to a guard bed comprises passing a first portion of the dehydrated feed stream from the regenerative dehydration zone to the guard bed in a first direction; and regenerating the spent Linde Type A molecular sieve in the regenerative dehydration zone comprises:
- heating a second portion of the dehydrated feed stream to form a regenerant; and
- passing the regenerant through the regenerative dehydration zone in a second direction opposite to the first direction, wherein the regenerant bypasses the guard bed.

* * * * *